United States Patent
Vorholt et al.

(10) Patent No.: US 10,377,057 B2
(45) Date of Patent: Aug. 13, 2019

(54) PROCESS FOR THE CONTINUOUS PREPARATION OF WATER-ABSORBENT POLYMERS

(71) Applicant: EVONIK DEGUSSA GMBH, Essen (DE)

(72) Inventors: Herbert Vorholt, Haltern am See (DE); Henry Rudolph, Krefeld (DE); Armin Reimann, Willich (DE); Volker Becker, Oberhausen (DE); Detlef Jung, Toenisvorst (DE); Manfred van Stiphoudt, Kempen (DE)

(73) Assignee: Evonik Degussa GmbH, Essen (DE)

( * ) Notice: Subject to any disclaimer, the term of this patent is extended or adjusted under 35 U.S.C. 154(b) by 605 days.

(21) Appl. No.: 14/364,346

(22) PCT Filed: Dec. 13, 2012

(86) PCT No.: PCT/EP2012/075358
§ 371 (c)(1),
(2) Date: Jun. 11, 2014

(87) PCT Pub. No.: WO2013/104479
PCT Pub. Date: Jul. 18, 2013

(65) Prior Publication Data
US 2014/0377538 A1    Dec. 25, 2014

(30) Foreign Application Priority Data
Jan. 12, 2012 (EP) ..................................... 12150875

(51) Int. Cl.
*B29B 9/02* (2006.01)
*B29B 9/12* (2006.01)
(Continued)

(52) U.S. Cl.
CPC ............. *B29B 13/065* (2013.01); *A61L 15/24* (2013.01); *A61L 15/60* (2013.01); *B29B 9/02* (2013.01);
(Continued)

(58) Field of Classification Search
None
See application file for complete search history.

(56) References Cited

U.S. PATENT DOCUMENTS 3,998,433 A    12/1976  Iwako
4,076,663 A    2/1978   Masuda et al.
(Continued)

FOREIGN PATENT DOCUMENTS

DE    2520788 A1    11/1975
DE    2617612 A1    11/1977
(Continued)

OTHER PUBLICATIONS

Buchholz, Frederick L. and Graham, Andrew T., "Modern Superabsorbent Polymer Technology," copyright 1998, John Wiley & Sons, Inc., Chapter 3: "Commercial Processes for the Manufacture of Superabsorbent Polymers," pp. 69-103 (40 pages).
(Continued)

*Primary Examiner* — Benjamin A Schiffman
(74) *Attorney, Agent, or Firm* — Bernard Lau; Jason S. Ngui; Linda S. Li (57) ABSTRACT

The invention relates generally to a process for the preparation of water-absorbent polymer particles, comprising the process steps including of drying the polymer gel particles wherein in process step (viii) the gel particles obtained in process step (vii) are charged onto the surface of the belt material of a belt dryer at a position $L_0$ and are subsequently dried on their way through the belt dryer and wherein the belt material has been cooled before coming into contact
(Continued)

with the gel particles. The invention also relates to water-absorbent polymer particles obtainable by such a process.

14 Claims, 3 Drawing Sheets

(51) Int. Cl.
| | |
|---|---|
| C08F 6/00 | (2006.01) |
| B29B 13/06 | (2006.01) |
| B29K 33/00 | (2006.01) |
| B29K 35/00 | (2006.01) |
| F26B 17/02 | (2006.01) |
| A61L 15/60 | (2006.01) |
| C08J 3/24 | (2006.01) |
| A61L 15/24 | (2006.01) |
| C08J 3/075 | (2006.01) |

(52) U.S. Cl.
CPC ............... *B29B 9/12* (2013.01); *C08F 6/008* (2013.01); *C08J 3/075* (2013.01); *C08J 3/245* (2013.01); *F26B 17/023* (2013.01); *B29K 2033/00* (2013.01); *B29K 2035/00* (2013.01); *C08J 2333/02* (2013.01); *Y10T 428/254* (2015.01); *Y10T 428/2998* (2015.01)

(56) References Cited

U.S. PATENT DOCUMENTS

| | | | |
|---|---|---|---|
| 4,179,367 A | | 12/1979 | Barthell et al. |
| 4,286,082 A | | 8/1981 | Tsubakimoto et al. |
| 4,587,308 A | | 5/1986 | Makita et al. |
| 4,857,610 A | | 8/1989 | Chmelir et al. |
| 4,893,999 A | | 1/1990 | Chmelir et al. |
| 5,409,771 A | | 4/1995 | Dahmen et al. |
| 5,610,220 A | | 3/1997 | Klimmek et al. |
| 5,672,633 A | | 9/1997 | Brehm et al. |
| 6,576,713 B2 | | 6/2003 | Ishizaki et al. |
| 6,620,889 B1 | | 9/2003 | Mertens et al. |
| 6,710,141 B1 | | 3/2004 | Heide et al. |
| 7,179,862 B2 | | 2/2007 | Mertens et al. |
| 7,285,599 B2 | | 10/2007 | Mertens et al. |
| 7,541,395 B2 | | 6/2009 | Reimann et al. |
| 7,572,864 B2 | | 8/2009 | Mertens et al. |
| 7,728,045 B2 | | 6/2010 | Becker et al. |
| 7,863,338 B2 | | 1/2011 | Becker et al. |
| 7,893,134 B2 | | 2/2011 | Reimann et al. |
| 8,119,755 B2 | | 2/2012 | Weismantel et al. |
| 8,349,913 B2 | | 1/2013 | Harren et al. |
| 8,445,596 B2 | | 5/2013 | Mertens et al. |
| 8,802,800 B2 | | 8/2014 | Fujino et al. |
| 8,809,475 B2 | | 8/2014 | Matsumoto et al. |
| 2004/0186229 A1 | | 9/2004 | Heide et al. |
| 2005/0059564 A1* | | 3/2005 | Li .................... C10M 111/04 508/532 |
| 2008/0021150 A1* | | 1/2008 | Becker .................. B01J 20/26 524/555 |
| 2008/0214749 A1 | | 9/2008 | Weismantel et al. |
| 2009/0105389 A1 | | 4/2009 | Walden et al. |
| 2009/0227741 A1 | | 9/2009 | Walden et al. |
| 2010/0010184 A1 | | 1/2010 | Weismantel et al. |
| 2012/0016084 A1 | | 1/2012 | Dairoku et al. |
| 2012/0302445 A1 | | 11/2012 | Rudolph et al. |

FOREIGN PATENT DOCUMENTS

| | | | | |
|---|---|---|---|---|
| DE | 2706135 | A1 | 8/1978 | |
| DE | 3503458 | A1 | 8/1985 | |
| DE | 3544770 | A1 | 6/1987 | |
| DE | 4020780 | C1 | 8/1991 | |
| DE | 4244548 | A1 | 7/1994 | |
| DE | 4418818 | A1 | 1/1995 | |
| DE | 4333056 | A1 | 3/1995 | |
| DE | 19909653 | A1 | 9/2000 | |
| DE | 10223060 | A1 | 12/2003 | |
| EP | 0228638 | A1 | 7/1987 | |
| EP | 0955086 | A1 | 11/1999 | |
| EP | 1683813 | A2 | 7/2006 | |
| JP | 2002-121291 | A | 4/2002 | |
| JP | WO 2010114058 | A1 * | 10/2010 | ............... C08J 3/12 |
| JP | 2011-527359 | A | 10/2011 | |
| JP | 2011-231255 | A | 11/2011 | |
| KR | 2007-0108281 | A | 11/2007 | |
| WO | 2001038402 | A1 | 5/2001 | |
| WO | 0222717 | A1 | 3/2002 | |
| WO | 02056812 | A2 | 7/2002 | |
| WO | 2010/114058 | A1 | 10/2010 | |
| WO | 2011/025013 | A1 | 3/2011 | |

OTHER PUBLICATIONS

Mujumdar, "Handbook of Industrial Drying," copyright 1995, Marcel Dekker, Inc., Chapter 16: "Conveyor Dryers," Sturgeon, S.T. Hudson Engineers, Inc., pp. 525-528 and 535 (7 pages).
Research Disclosure, "Drying of Pasty Materials Using a Continuous Through-Circulation Belt Dryer," copyright date unknown, disclosed anonymously, pp. 1-3 (3 pages).
Buchholz, Frederick L. and Graham, Andrew T., "Modern Superabsorbent Polymer Technology," copyright 1998, John Wiley & Sons, Inc., Chapter 1: "Absorbency and Superabsorbency," pp. 1-17 (19 pages).
Buchholz, Frederick L. and Graham, Andrew T., "Modern Superabsorbent Polymer Technology," copyright 1998, John Wiley & Sons, Inc., Chapter 2: "Chemistry of Superabsorbent Polyacrylates," pp. 19-67 (51 pages).
Buchholz, Frederick L. and Graham, Andrew T., "Modern Superabsorbent Polymer Technology," copyright 1998, John Wiley & Sons, Inc., Chapter 3: "Commercial Processes for the Manufacture of Superabsorbent Polymers," pp. 69-117 (51 pages).
Buchholz, Frederick L. and Graham, Andrew T., "Modern Superabsorbent Polymer Technology," copyright 1998, John Wiley & Sons, Inc., Chapter 4: "Analysis and Characterization of Superabsorbent Polymers," pp. 119-165 (49 pages).
Buchholz, Frederick L. and Graham, Andrew T., "Modern Superabsorbent Polymer Technology," copyright 1998, John Wiley & Sons, Inc., Chapter 5: "The Structure and Properties of Superabsorbent Polyacrylates," pp. 167-221 (57 pages).
International Search Report dated Apr. 2, 2013 in PCT/EP2012/075358 (4 pages).
Vorholt et al., U.S. Appl. No. 14/364,313, filed Jun. 11, 2014.
Written Opinion dated Apr. 2, 2013 in PCT/EP2012/075358 (9 pages).

* cited by examiner

PROCESS FOR THE CONTINUOUS PREPARATION OF WATER-ABSORBENT POLYMERS

This application is a national stage application under 35 U.S.C. § 371 of International Application No. PCT/EP2012/075358 filed 13 Dec. 2012, which claims priority to European Application No. EP 12150875.8 filed 12 Jan. 2012, the disclosures of which are expressly incorporated herein by reference.

FIELD

The invention relates to a process for the preparation of water-absorbent polymer particles, to water-absorbent polymer particles obtainable by such a process, to a composite material, to a process for the preparation of a composite material, to the composite material obtainable by such a process, to chemical products and to the use of the water-absorbent polymer particles or a composite material.

BACKGROUND

Superabsorbers are water-insoluble, crosslinked polymers which are able to absorb large amounts of aqueous fluids, especially body fluids, more especially urine or blood, with swelling and the formation of hydrogels, and to retain such fluids under a certain pressure. By virtue of those characteristic properties, such polymers are chiefly used for incorporation into sanitary articles, such as, for example, baby's nappies/diapers, incontinence products or sanitary towels.

The preparation of superabsorbers is generally carried out by free-radical polymerisation of acid-group-carrying monomers in the presence of crosslinkers, it being possible for polymers having different absorber properties to be prepared by the choice of the monomer composition, the crosslinkers and the polymerisation conditions and of the processing conditions for the hydrogel obtained after the polymerisation (for details see, for example, *Modern Superabsorbent Polymer Technology*, F L Buchholz, G T Graham, Wiley-VCH, 1998).

The acid-group-carrying monomers can be polymerized in the presence of the crosslinkers in a batch process or in a continuous process. An example for a continuous process for preparing superabsorbers is disclosed in U.S. Pat. No. 4,857,610. According to this process, an aqueous monomer solution containing acrylic acid and crosslinkers is continuously charged in a layer at least one centimeter thick on a moving endless conveyor belt and polymerized. The gel that is thus obtained is continuously discharged from the conveyor belt and is subsequently comminuted and dried to a water content of preferably less than 10 wt.-%.

Drying of the polymer gel particles is usually performed on a continuous belt dryer. US 2008/214749 A1 discloses a process for producing a water-absorbing polymers having a low Drying Quality Index by polymerizing a monomer solution, comprising at least one ethylenically unsaturated acid-functional monomer and at least one crosslinker, and drying the resulting hydrogel by means of a heated gas stream in a continuous belt dryer. According to this process a gas stream is flowed against the hydrogel upwardly in an upstream sector of a belt dryer and downwardly in a downstream sector of a belt dryer.

The upwardly directed flow of the hot drying gas onto the belt material in the upstream sector of the belt dryer in the process disclosed in US 2008214749 A1 heats the belt material to temperatures significantly above 180° C. However, the inventors of the present invention have discovered that if the gel particles are charged onto such a heated surface in the upstream sector of the belt dryer, this may lead to a product with insufficient and unreproducible properties. For example the color may change by charging the gel particles onto a belt surface that is to hot. Additionally the product may stick to the conveyor belt if the heat is too high at the location at which the gel is charged onto the belt.

SUMMARY

An object of the invention is to overcome at least a part of the above mentioned drawbacks of the prior art. A further object is to provide a process to prepare water-absorbent polymer particles with reproducible properties. Furthermore it is an object of the invention to produce water-absorbent polymer particles with reproducible colors.

A contribution to the solution of these objects is made by a process for the preparation of water-absorbent polymer particles, comprising the process steps of (i) preparing an aqueous monomer solution comprising at least partially neutralized, monoethylenically unsaturated monomers bearing carboxylic acid groups ($\alpha$1) and at least one crosslinker ($\alpha$3);

(ii) optionally adding fine particles of a water-absorbent polymer to the aqueous monomer solution;

(iii) adding a polymerization initiator or a at least one component of a polymerization initiator system that comprises two or more components to the aqueous monomer solution;

(iv) decreasing the oxygen content of the aqueous monomer solution;

(v) charging the aqueous monomer solution into a polymerization reactor;

(vi) polymerizing the monomers in the aqueous monomer solution in the polymerization reactor;

(vii) discharging the polymer gel strand out of the polymerization reactor and optionally comminuting the polymer gel thereby obtaining polymer gel particles;

(viii) drying the polymer gel particles;

(ix) grinding the dried polymer gel particles thereby obtaining particulate water-absorbent polymer particles;

(x) sizing the grinded water-absorbent polymer particles; and (xi) treating the surface of the grinded and sized water-absorbent polymer particles;

wherein in process step (viii) the gel particles obtained in process step (vii) are charged onto the surface of the belt material of a belt dryer at a position $L_0$ and are subsequently dried on their way through the belt dryer and wherein the belt material has been cooled before coming into with the gel particles. Preferably, the surface of the belt material of the belt dryer at position $L_0$ has been cooled to a temperature below 160° C., particular preferred below 140° C. and more preferred below 120° C. before coming into contact with the gel particles.

DETAILED DESCRIPTION

The process according to the present invention is preferably a continuous process in which the aqueous monomer solution is continuously provided and is continuously fed into the polymerization reactor. The hydrogel obtained is continuously discharged out of the polymerization reactor and is continuously comminuted, dried, grinded and classified in the subsequent process steps. This continuous process may, however, be interrupted in order to, for example, substitute certain parts of the process equipment, like the belt material of the conveyor belt if a conveyor belt is used as the polymerization reactor, clean certain parts of the process equipment, especially for the purpose of removing polymer deposits in tanks or pipes, or start a new process when water-absorbent polymer particles with other absorption characteristics have to be prepared.

Water-absorbent polymer particles which are preferred according to the invention are particles that have an average particle size in accordance with WSP 220.2 (test method of "Word Strategic Partners" EDANA and INDA) in the range of from 10 to 3,000 µm, preferably 20 to 2,000 µm and particularly preferably 150 to 850 µm. In this context, it is particularly preferable for the content of polymer particles having a particle size in a range of from 300 to 600 µm to be at least 30 wt.-%, particularly preferably at least 40 wt.-% and most preferably at least 50 wt.-%, based on the total weight of the water-absorbent polymer particles.

In process step (i) of the process according to the present invention an aqueous monomer solution containing partially neutralized, monoethylenically unsaturated monomers bearing carboxylic acid groups ($\alpha$1) and at least one crosslinker ($\alpha$3) is prepared.

Preferred monoethylenically unsaturated monomers bearing carboxylic acid groups ($\alpha$1) are those cited in DE 102 23 060 A1 as preferred monomers ($\alpha$1), whereby acrylic acid is particularly preferred.

It is preferred according to the present invention that the water-absorbent polymer produced by the process according to the invention comprises monomers bearing carboxylic acid groups to at least 50 wt. %, preferably to at least 70 wt. % and further preferably to at least 90 wt. %, based on the dry weight. It is particularly preferred according to the invention, that the water-absorbent polymer produced by the process according to the invention is formed from at least 50 wt. %, preferably at least 70 wt. % of acrylic acid, which is preferably neutralized to at least 20 mol %, particularly preferably to at least 50 mol %. The concentration of the partially neutralized, monoethylenically unsaturated monomers bearing carboxylic acid groups ($\alpha$1) in the aqueous monomer solution that is provided in process step (i) is preferably in the range between 10-60 wt.-%, preferably 20 to 50 wt.-% and most preferably between 30 to 40 wt.-%, based on the total weight of the aqueous monomer solution.

The aqueous monomer solution may also comprise monoethylenically unsaturated monomers ($\alpha$2) which are copolymerizable with ($\alpha$1). Preferred monomers ($\alpha$2) are those monomers which are cited in DE 102 23 060 A1 as preferred monomers ($\alpha$2), whereby acrylamide is particularly preferred.

Preferred crosslinkers ($\alpha$3) according to the present invention are compounds which have at least two ethylenically unsaturated groups in one molecule (crosslinker class I), compounds which have at least two functional groups which can react with functional groups of the monomers ($\alpha$1) or ($\alpha$2) in a condensation reaction (=condensation crosslinkers), in an addition reaction or a ring-opening reaction (cross-linker class II), compounds which have at least one ethylenically unsaturated group and at least one functional group which can react with functional groups of the monomers ($\alpha$1) or ($\alpha$2) in a condensation reaction, an addition reaction or a ring-opening reaction (crosslinker class III), or polyvalent metal cations (cross-linker class IV). Thus with the compounds of crosslinker class I a crosslinking of the polymer is achieved by radical polymerisation of the ethylenically unsaturated groups of the crosslinker molecules with the monoethylenically unsaturated monomers ($\alpha$1) or ($\alpha$2), while with the compounds of crosslinker class II and the polyvalent metal cations of crosslinker class IV a crosslinking of the polymer is achieved respectively via condensation reaction of the functional groups (crosslinker class II) or via electrostatic interaction of the polyvalent metal cation (crosslinker class IV) with the functional groups of the monomer ($\alpha$1) or ($\alpha$2). With compounds of cross-linker class III a cross-linking of the polymers is achieved correspondingly by radical polymerisation of the ethylenically unsaturated groups as well as by condensation reaction between the functional groups of the cross-linkers and the functional groups of the monomers ($\alpha$1) or ($\alpha$2).

Preferred crosslinkers ($\alpha$3) are all those compounds which are cited in DE 102 23 060 A1 as crosslinkers ($\alpha$3) of the crosslinker classes I, II, III and IV, whereby as compounds of crosslinker class I, N, N'-methylene bisacrylamide, polyethyleneglycol di(meth)acrylates, triallylmethylammonium chloride, tetraallylammonium chloride and allylnonaethyleneglycol acrylate produced with 9 mol ethylene oxide per mol acrylic acid are particularly preferred, and and as compounds of crosslinker class IV, $Al_2(SO_4)_3$ and its hydrates are particularly preferred.

Preferred water-absorbent polymers produced by the process according to the invention are polymers which are crosslinked by crosslinkers of the following crosslinker classes or by crosslinkers of the following combinations of crosslinker classes respectively: I, II, III, IV, III, I III, I IV, I II III, I II IV, I III IV, II III IV, II IV or III IV.

Further preferred water-absorbent polymers produced by the process according to the invention are polymers which are crosslinked by any of the crosslinkers disclosed in DE 102 23 060 A1 as crosslinkers of crosslinker classes I, whereby N,N'-methylene bisacrylamide, polyethyleneglycol di(meth)acrylates, triallyl-methylammonium chloride, tetraallylammonium chloride and allylnonaethylene-glycol acrylate produced from 9 mol ethylene oxide per mol acrylic acid are particularly preferred as crosslinkers of crosslinker class I.

The aqueous monomer solution may further comprise water-soluble polymers ($\alpha$4). Preferred water-soluble polymers ($\alpha$4) include partly or completely saponified polyvinyl alcohol, polyvinylpyrrolidone, starch or starch derivatives, polyglycols or polyacrylic acid. The molecular weight of these polymers is not critical, as long as they are water-soluble. Preferred water-soluble polymers ($\alpha$4) are starch or starch derivatives or polyvinyl alcohol. The water-soluble polymers ($\alpha$4), preferably synthetic, such as polyvinyl alcohol, can not only serve as a graft base for the monomers to be polymerized. It is also conceivable for these water-soluble polymers to be mixed with the hydrogel or the already dried, water-absorbent polymer.

The aqueous monomer solution can furthermore also comprise auxiliary substances ($\alpha$5), these auxiliary substances including, in particular, complexing agents, such as, for example, EDTA.

The relative amount of monomers ($\alpha$1) and ($\alpha$2) and of crosslinking agents ($\alpha$3) and water-soluble polymers ($\alpha$4) and auxiliary substances ($\alpha$5) in the aqueous monomer solution is preferably chosen such that the water-absorbent polymer structure obtained in process step x) after drying is based to the extent of 20-99.999 wt.-%, preferably to the extent of 55-98.99 wt.-% and particularly preferably to the extent of 70-98.79 wt.-% on monomers ($\alpha$1), to the extent of 0-80 wt.-%, preferably to the extent of 0-44.99 wt.-% and particularly preferably to the extent of 0.1-44.89 wt.-% on the monomers (α2), to the extent of 0-5 wt.-%, preferably to the extent of 0.001-3 wt.-% and particularly preferably to the extent of 0.01-2.5 wt.-% on the crosslinking agents (α3), to the extent of 0-30 wt.-%, preferably to the extent of 0-5 wt.-% and particularly preferably to the extent of 0.1-5 wt.-% on the water-soluble polymers (α4), to the extent of 0-20 wt.-%, preferably to the extent of 0-10 wt.-% and particularly preferably to the extent of 0.1-8 wt.-% on the auxiliary substances (α5), and to the extent of 0.5-25 wt.-%, preferably to the extent of 1-10 wt.-% and particularly preferably to the extent of 3-7 wt.-% on water (α6)

the sum of the amounts by weight (α1) to (α6) being 100 wt.-%.

Optimum values for the concentration in particular of the monomers, crosslinking agents and water-soluble polymers in the monomer solution can be determined by simple preliminary experiments or from the prior art, in particular the publications U.S. Pat. No. 4,286,082, DE 27 06 135 A1, U.S. Pat. No. 4,076,663, DE 35 03 458 A1, DE 40 20 780 C1, DE 42 44 548 A1, DE 43 33 056 A1 and DE 44 18 818 A1.

In process step (ii) fine particles of a water-absorbent polymer may optionally be added to the aqueous monomer solution.

Water-absorbent fine particles are preferably water-absorbent polymer particles the composition of which corresponds to the composition of the above described water-absorbent polymer particles, wherein it is preferred that at least 90 wt.-% of the water-absorbent fine particles, preferably at least 95 wt.-% of the water-absorbent fine particles and most preferred at least 99 wt.-% of the water-absorbent polymer particles have a particle size of less than 200 μm, preferably less than 150 μm and particular preferably less than 100 μm.

In a preferred embodiment of the process according to the present invention the water-absorbent fine particles which may optionally be added to the aqueous monomer solution in process step (ii) are fine particles which are obtained in process step (x) of the process according to the present invention and which are thus recycled.

The fine particles can be added to the aqueous monomer solution by means of any mixing device the person skilled of the art would consider as appropriate for this purpose. In a preferred embodiment of the present invention, which is especially useful if the process is performed continuously as described above, the fine particles are added to the aqueous monomer solution in a mixing device in which a first stream of the fine particles and a second stream of the aqueous monomer solution are directed continuously, but from different directions, onto a rotating mixing device. Such a kind of mixing setup can be realised in a so called "Rotor Stator Mixer" which comprise in their mixing area a preferably cylindrically shaped, non-rotating stator, in the centre of which a likewise preferably cylindrically shaped rotor is rotating. The walls of the rotor as well as the walls of the stator are usually provided with notches, for example notches in the form of slots, through which the mixture of fine particles and aqueous monomer solution can be sucked through and thus can be subjected to high shear forces.

In this context it is particularly preferred that the first stream of the fine particles an the second stream of the aqueous monomer solution form an angle δ in the range from 60 bis 120°, more preferred in the range from 75 bis 105°, even more preferably in the range from 85 bis 95° and most preferred from an angle of about 90°. It is also preferred that the stream of the mixture of fine particles and aqueous monomer solution that leaves the mixer and the first stream of fine particles that enters the mixer form an angle ε in the range from 60 bis 120°, preferably in the range from 75 bis 105°, even more preferred in the range from 85 bis 95° and most preferred form an angle of about 90°.

Such a kind of mixing set up can, for example, be realized by means of mixing devices which are disclosed in DE-A-25 20 788 and DE-A-26 17 612, the content of which is incorporated herein by reference. Concrete examples of mixing devices which can be used to add the fine particles to the aqueous monomer solution in process step (ii) of the present invention are the mixing devices which can be obtained by the IKA® Werke GmbH & Co. KG, Staufen, Germany, under designations MHD 2000/4, MHD 2000/05, MHD 2000/10, MDH 2000/20, MHD 2000/30 and MHD 2000/50, wherein the mixing device MHD 2000/20 is particularly preferred. Further mixing devices which can be used are those offered by ystral GmbH, Ballrechten-Dottingen, Germany, for example under designation "Conti TDS", or by Kinematika AG, Luttau, Switzerland, for example under the trademark Megatron®.

The amount of fine particles that may be added to the aqueous monomer solution in process step (ii) is preferably in the range from 0.1 to 15 wt.-%, even more preferred in the range from 0.5 to 10 wt.-% Gew.-% and most preferred in the range from 3 to 8 wt.-%, based in the weight of the aqueous monomer solution.

In process step (iii) of the process according to the present invention a polymerization initiator or at least one component of a polymerization initiator system that comprises two or more components is added to the aqueous monomer solution.

As polymerization initiators for initiation of the polymerisation all initiators forming radicals under the polymerisation conditions can be used, which are commonly used in the production of superabsorbers. Among these belong thermal catalysts, redox catalysts and photo-initiators, whose activation occurs by energetic irradiation. The polymerisation initiators may be dissolved or dispersed in the aqueous monomer solution. The use of water-soluble catalysts is preferred.

As thermal initiators may be used all compounds known to the person skilled in the art that decompose under the effect of temperature to form radicals. Particularly preferred are thermal polymerisation initiators with a half life of less than 10 seconds, more preferably less than 5 seconds at less that 180° C., more preferably at less than 140° C. Peroxides, hydroperoxides, hydrogen peroxide, persulfates and azo compounds are particularly preferred thermal polymerisation initiators. In some cases it is advantageous to use mixtures of various thermal polymerisation initiators. Among such mixtures, those consisting of hydrogen peroxide and sodium or potassium peroxodisulfate are preferred, which may be used in any desired quantitative ratio. Suitable organic peroxides are preferably acetylacetone peroxide, methyl ethyl ketone peroxide, benzoyl peroxide, lauroyl peroxide, acetyl peroxide, capryl peroxide, isopropyl peroxidicarbonate, 2-ethylhexyle peroxidicarbonate, tert.-butyl hydroperoxide, cumene hydroperoxide, tert.-amyl perpivalate, tert.-butyl perpivalate, tert.-butyl perneohexonate, tert.-butyl isobutyrate, tert.-butyl per-2-ethylhexenoate, tert.-butyl perisononanoate, tert.-butyl permaleate, tert.-butyl perbenzoate, tert.-butyl-3,5,5-trimethylhexanoate and amyl perneodecanoate. Furthermore, the following thermal polymerisation initiators are preferred: azo compounds such as azo-bis-isobutyronitrol, azo-bis-dimethylvaleronitril, 2,2-azobis-(2-amidinopropane)dihydrochloride, azo-bis-ami-dinopropane dihydrochloride, 2,2'-azobis-(N,N-dimethylene) isobutyramidine di-hydrochloride, 2-(carbamoylazo) isobutyronitrile and 4,4'-azobis-(4-cyano-valeric acid). The aforementioned compounds are used in conventional amounts, preferably in a range from 0.01 to 5, more preferably 0.1 to 2 mol %, respectively based upon the amount of the monomers to be polymerised.

Redox catalyst comprise two of more components, usually one or more of the peroxo compounds listed above, and at least one reducing component, preferably ascorbic acid, glucose, sorbose, mannose, ammonium or alkali metal hydrogen sulfite, sulfate, thiosulfate, hyposulfite or sulfide, metal salts such as iron II ions or silver ions or sodium hydroxymethyl sulfoxylate. Preferably ascorbic acid or sodium pyrosulfite is used as reducing component of the redox catalyst. $1 \times 10^{-5}$ to 1 mol % of the reducing component of the redox catalyst and $1 \times 10^{-5}$ to 5 mol % of the oxidising component of the redox catalyst are used, in each case referred to the amount of monomers used in the polymerisation. Instead of the oxidising component of the redox catalyst, or as a complement thereto, one or more, preferably water-soluble azo compounds may be used.

If the polymerisation is initiated by action of energetic beams, so-called photo-initiators are generally used as initiator. These can comprise for example so-called α-splitters, H-abstracting systems or also azides. Examples of such initiators are benzophenone derivatives such as Michlers ketone, phenanthrene derivatives, fluorine derivatives, anthraquinone derivatives, thioxanthone derivatives, cumarin derivatives, benzoinether and derivatives thereof, azo compounds such as the above-mentioned radical formers, substituted hexaarylbisimidazoles or acylphosphine oxides. Examples of azides are: 2-(N,N-dimethylamino) ethyl-4-azidocinnamate, 2-(N,N-dimethylamino)ethyl-4-azidonaphthylketone, 2-(N,N-di-methylamino)ethyl-4-azidobenzoate, 5-azido-1-naphthyl-2'-(N,N-dimethylamino) ethylsulfone, N-(4-sulfonylazidophenyl)maleinimide, N-acetyl-4-sulfonyl-azidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis (p-azidobenzylidene)-4-methylcyclohexanone. The photo-initiators, when used, are generally employed in quantities from 0.01 to 5 wt.-% based on the monomers to be polymerised.

A particularly preferred redox system that is used in the process according to the present invention is a redox system comprising hydrogen peroxide, sodium peroxodisulfate and ascorbic acid.

In this context it should also be noted that the polymerization initiator may be added before, during or after process step (iv), i.e. after the oxygen content of the aqueous monomer solution has been decreased. If a polymerisation initiator system is used that comprises two or more components, like the preferred initiator system that comprises hydrogen peroxide, sodium peroxodisulfate and ascorbic acid and that is active only if all the components have been added, one or more of the components of such a polymerisation initiator system may, for example, be added before process step (iv), whereas the remaining component or the remaining components which are necessary to complete the activity of the polymerisation initiator system, are added after process step (iv), perhaps even after process step (v).

In process step (iv) of the process according to the present invention the oxygen content of the aqueous monomer solution is decreased, whereby it should be mentioned that process step (iv) can also be performed before, during or after process step (ii). Preferably, the oxygen content of the aqueous monomer solution is decreased after the fine particles have been added in process step (ii).

The oxygen content of the aqueous monomer solution is decreased by bringing the aqueous monomer solution into contact with an inert gas, such as nitrogen. The phase of the inert gas being in contact with the aqueous monomer solution is free of oxygen and is thus characterized by a very low oxygen partial pressure. As a consequence oxygen converts from the aqueous monomer solution into the phase of the inert gas until the oxygen partial pressures in the phase of the inert gas and the aqueous monomer solution are equal. Bringing the aqueous monomer phase into contact with a phase of an inert gas can be accomplished, for example, by introducing bubbles of the inert gas into the monomer solution in cocurrent, countercurrent or intermediate angles of entry. Good mixing can be achieved, for example, with nozzles, static or dynamic mixers or bubble columns. The oxygen content of the monomer solution before the polymerization is preferably lowered to less than 1 ppm by weight, more preferably to less than 0.5 ppm by weight.

In process step (v) of the process according to the present invention the aqueous monomer solution is charged into a polymerization reactor, preferably onto a conveyor belt, especially preferred at an upstream position of the conveyor belt and in process step (vi) the monomers in the aqueous monomer solution are polymerized in the polymerization reactor, thereby obtaining a polymer gel. If polymerization is performed on a polymerization belt as the polymerization reactor, a polymer gel strand is obtained in a downstream portion of the conveyor belt, which, before drying, is preferably comminuted in order to obtain gel particles.

As the polymerization reactor every reactor can be used which the person skilled in the art would regard as appropriate for the continuous or batchwise polymerization of monomers like acrylic acid in aqueous solutions. An example of a suitable polymerization reactor is a kneading reactor. In a kneader the polymer gel formed in the polymerization of the aqueous monomer solution is comminuted continuously by, for example, contrarotatory stirrer shafts, as described in WO 2001/38402.

Another example of a preferred polymerization reactor is a conveyor belt. As a conveyor belt that is useful for the process according to the present invention any conveyor belt can be used which the person skilled in the art considers to be useful as a support material onto which the above described aqueous monomer solution can be charged and subsequently polymerized to form a hydrogel. Examples of conveyor belts which can be used in the process according to the present invention are disclosed in DE-A-35 44 770, EP-A-0 955 086 and EP-A-1 683 813, the disclosure of which is incorporated herein by reference.

The conveyor belt usually comprises an endless moving conveyor belt passing over supporting elements and at least two guide rollers, of which at least one is driven and one is configured so as to be adjustable. Optionally, a winding and feed system for a release sheet that may be used in sections on the upper surface of the conveyor belt is provided. The system includes a supply and metering system for the reaction components, and optional irradiating means arranged in the direction of movement of the conveyor belt after the supply and metering system, together with cooling and heating devices, and a removal system for the polymer gel strand that is arranged in the vicinity of the guide roller for the return run of the conveyor belt. In order to provide for the completion of polymerization with the highest possible space-time yield, according to the present invention, in the vicinity of the upper run of the conveyor belt on both sides of the horizontal supporting elements, starting in the area of the supply and metering systems, there are upwardly extending supporting elements, the longitudinal axes of which intersect at a point that is beneath the upper run, and which shape the conveyor belt that is supported by them so that it become suitably trough-shaped. Thus, according to the present invention, the conveyor belt is supported in the vicinity of the supply system for the reaction components by a plurality of trough-shaped supporting and bearing elements that form a deep trough-like or dish-like configuration for the reaction components that are introduced. The desired trough-like shape is determined by the shape and arrangement of the supporting elements along the length of the path of the upper run.

In the area where the reaction components are introduced, the supporting elements should be relatively close to each other, whereas in the subsequent area, after the polymerization has been initiated, the supporting elements can be arranged somewhat further apart. Both the angle of inclination of the supporting elements and the cross-section of the supporting elements can be varied in order to flatten out the initially deep trough towards the end of the polymerization section and once again bring it to an extended state. In a further embodiment of the invention, each supporting element is preferably formed by a cylindrical or spherical roller that is rotatable about its longitudinal axis. By varying both the cross-section of the roller as well as the configuration of the roller it is easy to achieve the desired cross-sectional shape of the trough. In order to ensure proper formation of the trough by the conveyor belt, both when it makes the transition from a flat to a trough-like shape and when it is once again returned to the flat shape, a conveyor belt that is flexible in both the longitudinal and the transverse directions is preferred.

In process step (vii) of the process according to the present invention the particulate polymer gel that is obtained in the polymerization reactor, preferably the polymer gel particles obtained in the kneading reactor or the polymer gel strand obtained in the downstream portion of the conveyor belt, is/are discharged out of the reactor and is/are, especially in the case of the polymer gel strand obtained on the conveyor belt, (further) comminuted, thereby obtaining polymer gel particles. Preferably, the resulting polymer gel strand is removed from the conveyor belt as a continuous strand that is of a soft semi-solid consistency and is then passed on for further processing such as comminution.

Comminution of the polymer gel strand is preferably performed in at least three steps:
  in a first step, a cutting unit, preferably a knife, for example a knife as disclosed in WO-A-96/36464, is used for cutting the polymer gel strand into flat gel strips, preferably with a length within the range of 5 to 500 mm, preferably from 10 to 300 mm and particularly preferably from 100 to 200 mm, a height within the range from 1 to 30 mm, preferably from 5 to 25 mm and particularly preferably from 10 to 20 mm as well as a width within the range from 1 to 500 mm, preferably from 5 to 250 mm and particularly preferably from 10 to 200 mm;
  in a second step, a shredding unit, preferably a breaker, is used for shredding the gel strips into gel pieces, preferably with a length within the range of 2.5 to 25 mm, preferably from 1 to 12.5 mm, a height within the range from 0.5 to 15 mm, preferably from 0.25 to 7.5 mm as well as a width within the range from 0.5 to 20 mm, preferably from 0.25 to 10 mm and
  in a third step a "wolf" (grinding) unit, preferably a wolf, preferably having a screw and a whole plate, whereby the screw conveys against the whole plate is used in order to grind and crush gel pieces into polymer gel particles which are preferably smaller than the gel pieces.

An optimal surface-volume ratio is achieved hereby, which has an advantageous effect on the drying behaviour in process step (viii). A gel which has been comminuted in this way is particularly suited to belt drying. The three-step comminution offers a better "airability" because of the air channels located between the granulate kernels.

According to a particular embodiment of the process according to the present invention the carboxylic acid groups in the polymer gel that is obtained in process step (vii) and that is charged onto the belt material in process step (viii) are neutralized to an extend of less than 70 mol-%, preferably less than 67.5 mol-% and most preferably less than 65 mol. %.

In process step (viii) of the process according to the present invention the polymer gel particles are dried.

The drying of the polymer gel particles is takes place in a belt drier. A belt dryer is a convective system of drying, for the particularly gentle treatment of through-airable products. The product to be dried is placed onto an endless conveyor belt which lets gas through, and is subjected to the flow of a heated gas stream, preferably air. The drying gas is recirculated in order that it may become very highly saturated in the course of repeated passage through the product layer. A certain fraction of the drying gas, preferably not less than 10%, more preferably not less than 15% and most preferably not less than 20% and preferably up to 50%, more preferably up to 40% and most preferably up to 30% of the gas quantity per pass, leaves the dryer as a highly saturated vapor and carries off the water quantity evaporated from the product. The temperature of the heated gas stream is preferably not less than 50° C., more preferably not less than 100° C. and most preferably not less than 150° C. and preferably up to 250° C., more preferably up to 220° C. and most preferably up to 200° C.

The size and design of the dryers depends on the product to be processed, the manufacturing capacity and the drying duty. A belt dryer can be embodied as a single-belt, multi-belt, multi-stage or multistory system. The present invention is preferably practiced using a belt dryer having at least one belt. One-belt dryers are very particularly preferred. To ensure optimum performance of the belt-drying operation, the drying properties of the water-absorbent polymers are individually determined as a function of the processing parameters chosen. The hole size and mesh size of the belt is conformed to the product. Similarly, certain surface enhancements, such as electropolishing or Teflonizing, are possible.

The polymer gel particles to be dried are preferably applied to the belt of the belt dryer by means of a swivel belt. The feed height, i.e., the vertical distance between the swivel belt and the belt of the belt dryer, is preferably not less than 10 cm, more preferably not less than 20 cm and most preferably not less than 30 cm and preferably up to 200 cm, more preferably up to 120 cm and most preferably up to 40 cm. The thickness on the belt dryer of the polymer gel particles to be dried is preferably not less than 2 cm, more preferably not less than 5 cm and most preferably not less than 8 cm and preferably not more than 20 cm, more preferably not more than 15 cm and most preferably not more than 12 cm. The belt speed of the belt dryer is preferably not less than 0.005 m/s, more preferably not less than 0.01 m/s and most preferably not less than 0.015 m/s and preferably up to 0.05 m/s, more preferably up to 0.03 m/s and most preferably up to 0.025 m/s.

Furthermore, it is preferable according to the invention that the polymer gel particles are dried to a water content of from 0.5-25 wt.-%, preferably 1-10 wt.-% and particularly preferably 3-7 wt.-%.

In process step (ix) of the process according to the present invention the dried polymer gel particles are ground thereby obtaining particulate water-absorbent polymer particles.

For grinding of the dried polymer gel particles any device can be used the person skilled in the art considers as appropriate for grinding the above described dried polymer particles. As an example for a suitable grinding device a single- or multistage roll mill, preferably a two- or three-stage roll mill, a pin mill, a hammer mill or a vibratory mill may be mentioned.

In process step (x) of the process according to the present invention the ground water-absorbent polymer particles are sized, preferably using appropriate sieves. In this context it is particularly preferred that after sizing the water-absorbent polymer particles the content of polymer particles having a particle size of less than 150 μm is less than 10 wt.-%, preferably less than 8 wt.-% and particularly less than 6 wt.-% and that the content of polymer particles having a particle size of more than 850 μm is also less than 10 wt.-%, preferably less than 8 wt.-% and particularly less than 6 wt.-%. It is also preferred that after sizing the water-absorbent polymer particles at least 30 wt.-%, more preferred at least 40 wt.-% and most preferred at least 50 wt.-%, based on the total weight of the water-absorbent polymer particles, of the particles have a particle size in a range of from 300 to 600 μm.

In process step (xi) of the process according to the present invention the surface of the ground and sized water-absorbent polymer particles may be treated. As measures to treat the surface of water-absorbent polymer particles any measure can be used the person skilled in the art considers as appropriate for such a purpose. Examples of surface treatments include, for example, surface crosslinking, the treatment of the surface with water-soluble salts, such as aluminium sulfate or aluminium lactate, the treatment of the surface with inorganic particles, such as silicon dioxide, and the like. Preferably, the components used to treat the surface of the polymer particles (cross-linker, water soluble salts) are added in the form of aqueous solutions to the water-absorbent polymer particles. After the particles have been mixed with the aqueous solutions, they are heated to a temperature in the range from 150 to 230° C., preferably 160 to 200° C. in order to promote the surface-crosslinking reaction.

The process according to the present invention is characterized in that in process step (viii) the gel particles obtained in process step (vii) are charged onto the surface of the belt material of the belt dryer at a position $L_0$ and are subsequently dried on their way through the belt dryer and wherein the belt material has been cooled, preferably has been cooled to a temperature below 160° C., more preferably below 140° C. and most preferably below 120° C. before coming into contact with the gel particles.

Figure 1:
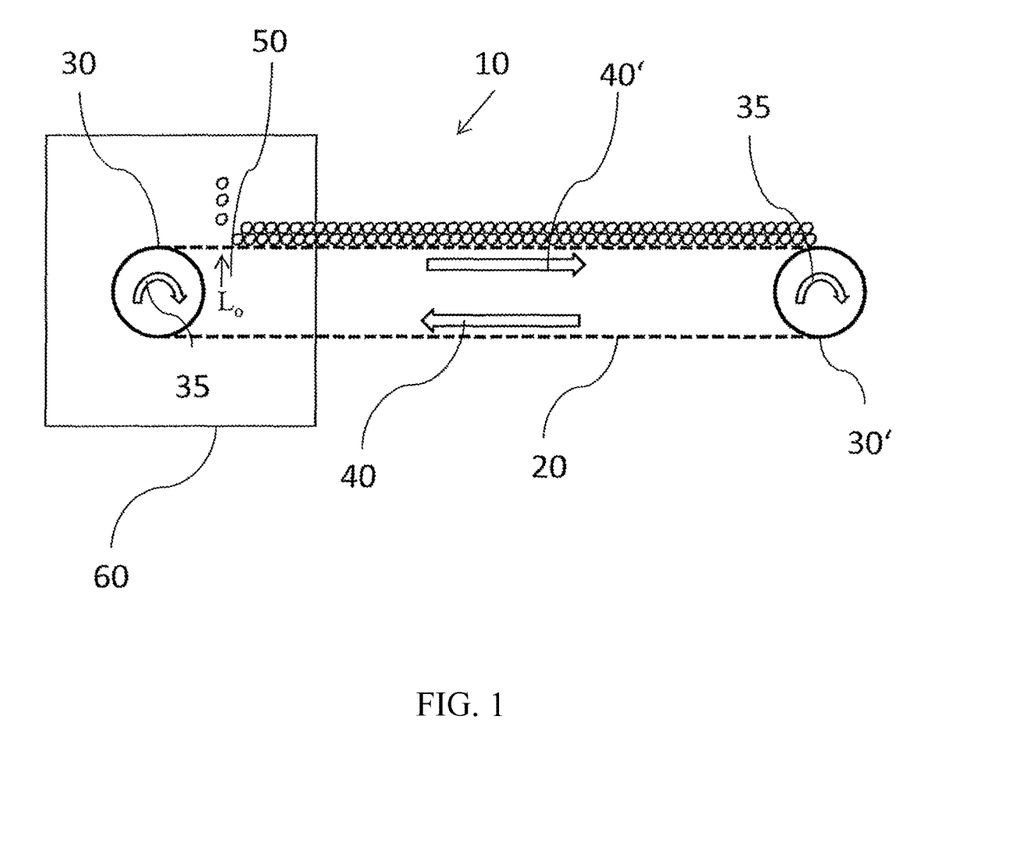
FIG. 1: Scheme of a conveyor belt with polymer gel on it.

Usually, a continuously operated belt dryer comprises a belt material that is continuously guided over a pair of guide rollers that are rotating in the same direction. Thus, the upper part of the belt material is transported in a direction from position $L_0$ towards the downstream portion of the belt dryer and the lower part of the belt is transported from the downstream portion towards position $L_0$, as shown in FIG. 1. As a consequence of this continuous transport of the belt material in the belt dryer the belt material is constantly heated to the drying temperature in the belt dryer, especially if the hot drying gas flows in an upward direction onto the belt material in the upstream sector of the belt dryer in the process disclosed in US 2008214749 A1.

In order to make sure that the temperature of the belt material at position $L_0$ is below the above mentioned maximum temperatures, it is therefore preferred that the surface of the belt material of the belt dryer has been cooled to a temperature below 160° C., more preferably below 140° C. and most preferably below 120° C. before the surface of the belt material comes into contact with the polymer gel at a position $L_0$ in process step (viii).

One reason of cooling of the belt material before it comes into contact with the gel particles is to provide a polymer material that might be processed more easily afterwards. For example, the shape of the dried polymer gel is in the form of shelves or sheets that might be more easily released from the surface of the belt material and might be handled more easily in the further process of for example grinding the polymer gel like in process step (ix). By cooling the surface of the belt material before it comes into contact with the polymer gel in process step (viii) it can be avoided that the gel particles firmly stick onto the belt material. Moreover, a disadvantageous colouring of the dried gel obtained in the gel dryer can be minimized by cooling the surface of the belt material at position $L_0$ to the temperatures previously defined.

The surface of the belt material might be cooled by contacting it with any material that is able to decrease the temperature of the belt material at or before the charging position $L_0$. For this purpose a cooling material might be used that can comprise solids, fluids or gases or at least two of those. The cooling material should be cooler than the belt surface to be cooled. As the belt material often reaches temperatures of more than 100° C., the use of water in its different physical conditions might be advantageous for cooling the belt material.

One possibility of cooling the surface of the belt material might be to continuously spray a cooling liquid, preferably water, more preferred water having a temperature in the range from 10 to 30° C., onto the surface of the belt material, preferably at least one position at or before the charging position $L_0$. The belt material also might be lead through a bath of a cooling liquid, preferably through a bath of water, more preferably through a bath of water having a temperature in the range from 10 to 30° C. The surface of the belt material also might be cooled by different fluids like alcohols, or mixtures of alcohols with water. Additionally or alternatively, a cooling flow of gas, like cooled air or cooled $CO_2$ or $N_2$ or mixtures thereof, might be used to cool down the belt before the polymer gel is charged onto the belt at the charging position $L_0$.

Another possibility of cooling the surface of the belt material might be to continuously spray an aqueous additive solution onto the belt material. The aqueous additive solution might, for example, be a mixture of water with an additive such as a polyalkylene glycol, in particular a polyethylene glycol with a molecular weight in the range from 100 to 20,000 g/mol, particular preferred in the range from 300 to 10,000 g/mol.

The concentration of the additive in the aqueous additive solution, in particular the concentration of the above mentioned polyalkylene glycols, is preferably in the range of 0.01 to 20 wt.-%, preferably in the range of 0.1 to 15 wt.-% and most preferred in the range from 1 to 5 wt.-%, based on the weight of the aqueous additive solution. The temperature of the aqueous additive solution is preferably in the range from 10 to 30° C.

The spraying of the cooling liquid, preferably the water, or the aqueous additive solution might be established by a nozzle that may be located at any position from which the surface of the belt material prior to the addition of the gel particles can be reached. If, as disclosed in Research Disclosure 374041, an oscillating belt distributor (swivel belt) is used, the nozzle may also be attached to this distributor.

A contribution to the solution of the objects mentioned at the beginning is also made by water-absorbent polymer particles which are obtainable by such a process. Preferably, these water-absorbent polymer particles are characterized by a residual monomer content of less than 500 ppm, preferably less than 450 ppm and even more preferably of less than 400 ppm, determined according to test method WSP 210.2.

A further contribution to achieving the objects described at the beginning is made by a composite material comprising the water-absorbent polymer particles obtainable by the process according to the present invention and a substrate. In this context, it is preferable for the water-absorbent polymer particles and the substrate to be firmly bonded to one another. Preferred substrates are films of polymers, such as, for example, of polyethylene, polypropylene or polyamide, metals, nonwovens, fluff, tissues, woven fabric, natural or synthetic fibres, or other foams. It is furthermore preferable according to the invention for the composite material to include at least one region which comprises the water-absorbent polymer particles in an amount in the range of from about 15 to 100 wt. %, preferably about 30 to 100 wt. %, particularly preferably from about 50 to 99.99 wt. %, furthermore preferably from about 60 to 99.99 wt. % and moreover preferably from about 70 to 99 wt. %, in each case based on the total weight of the composite material region in question, this region preferably having a size of at least 0.01 cm$^3$, preferably at least 0.1 cm$^3$ and most preferably at least 0.5 cm$^3$.

In a particularly preferred embodiment of the composite material according to the invention, this is a planar composite material such as is described as "absorbent material" in WO 02/056812 A1. The disclosure content of WO 02/056812 A1, in particular with respect to the precise structure of the composite material, the weight per unit area of its constituents and its thickness, is introduced herewith as reference and represents a part of the disclosure of the present invention.

A further contribution to achieving the objects mentioned at the beginning is made by a process for the production of a composite material, wherein the water-absorbent polymer particles obtainable by the process according to the present invention and a substrate and optionally an additive are brought into contact with one another. Substrates which are employed are preferably those substrates which have already been mentioned above in connection with the composite material according to the invention.

A contribution to achieving the objects mentioned at the beginning is also made by a composite material obtainable by the process described above, this composite material preferably having the same properties as the composite material according to the invention described above.

A further contribution to achieving the objects mentioned at the beginning is made by chemical products comprising the water-absorbent polymer particles obtainable by the process according to the present invention or a composite material according to the invention. Preferred chemical products are, in particular, foams, shaped articles, fibres, foils, films, cables, sealing materials, liquid-absorbing hygiene articles, in particular nappies and sanitary towels, carriers for plant or fungal growth-regulating agents or plant protection active compounds, additives for building materials, packaging materials or soil additives.

The use of the water-absorbent polymer particles obtainable by the process according to the present invention or of the composite material according to the present invention in chemical products, preferably in the abovementioned chemical products, in particular in hygiene articles, such as nappies or sanitary towels, and the use of the superabsorber particles as carriers for plant or fungal growth-regulating agents or plant protection active compounds also make a contribution to achieving the abovementioned objects. In the use as a carrier for plant or fungal growth-regulating agents or plant protection active compounds, it is preferable for the plant or fungal growth-regulating agents or plant protection active compounds to be able to be released over a period of time controlled by the carrier.

The invention is now more closely illustrated by figures, test methods and non-limiting examples.

FIG. 1 shows a conveyor belt system 10 with an endless moving conveyor belt 20 passing over two guide rollers 30, 30' of which at least one is driven. In this case the right guide roller 30' is driven because it is easier to pull the charged part of the belt than to push it. This is indicated by the circled arrow 35 in the centre of the guide roller 30'. The direction of the movement of the belt 20 is indicated by the hollow arrows 40, 40'. The upper part of the belt 20 is pulled to the right, as indicated by arrow 40, whereas the lower part of the belt 20 is pushed to the left, as indicated by arrow 40'. The massive arrow shows the charging position L$_0$ 50 where the polymer gel is charged onto the belt 20.

Figure 2:
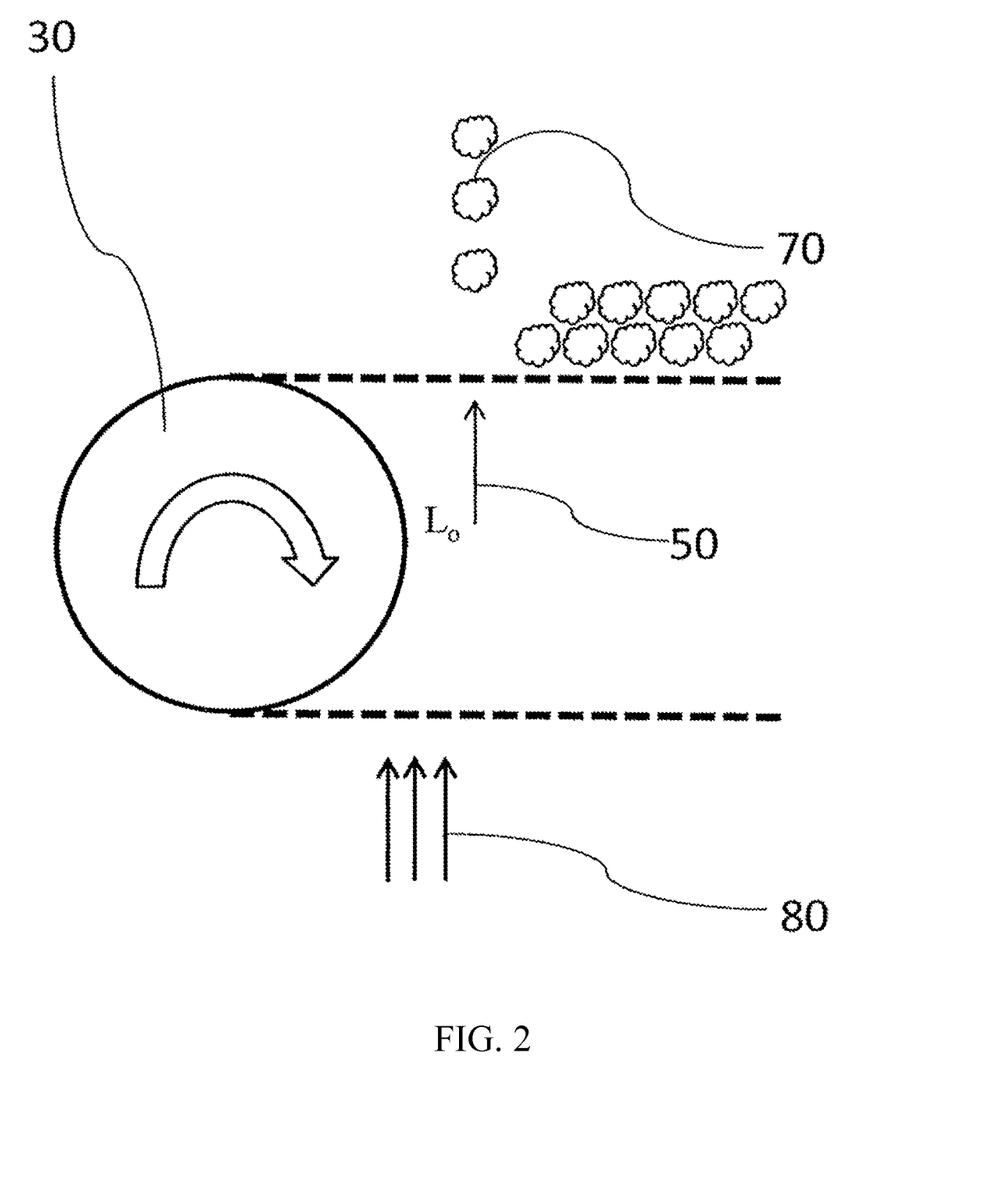
FIG. 2: Scheme of a part of the conveyor belt seen in FIG. 1 with cooling the belt material before the polymer gel is charged onto the belt.

In FIG. 2 a cut-out of FIG. 1 showing the part of the belt surrounded by line 60. Here the charging position L$_0$ 50 together with the guide roller 30 is shown. Additionally to FIG. 1 in FIG. 2 a cooling material 80 is indicated by three parallel arrows. This cooling material 80 is applied in this case by spraying water onto the surface of the belt material at the lower part of the belt at a position close to guide roller 30. As already mentioned, the cooling material 80 may also be applied by a cooling gas like cooled air or cooled $CO_2$ or $N_2$ or mixtures thereof. There also might be used a cooling gas together with a cooling solid like ice or a cooling fluid like water. The cooling material might be applied on one side of the conveyor belt 10 or on both sides. It would also be possible to install a cooling mechanism into the guide roller 30 to indirectly cool the belt 20. This would have the advantage that the belt 20 does not come into contact with the cooling material itself. The cooling material 80 might comprise components that simplify the discharging of the polymer gel after drying on the conveyor belt 20. The conveyor belt 20 might be heated after the polymer gel 70 is charged onto it.

Figure 3:
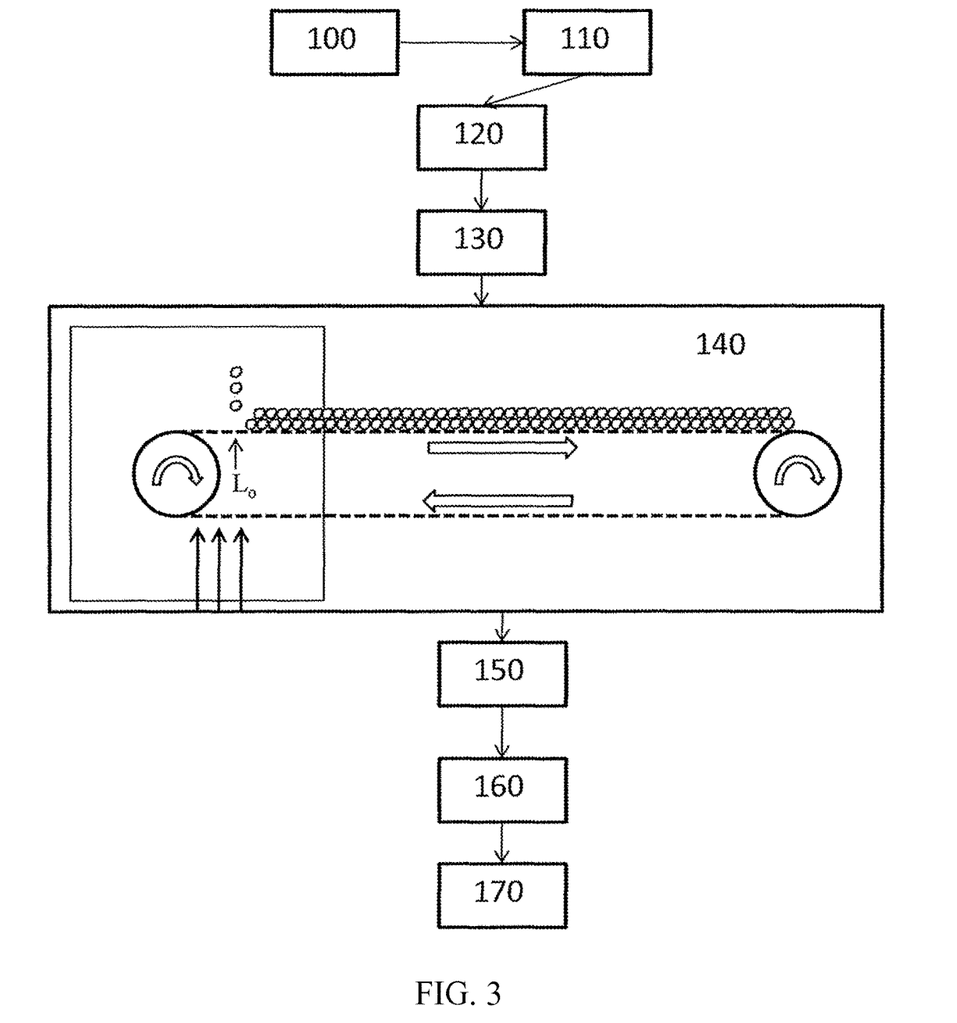
FIG. 3: Scheme of a part of the process flow to produce a water-absorbent polymer.

FIG. 3 shows a scheme of a process flow for the production of water-absorbent polymers in cross-section. In the first step 100 an aqueous monomer solution comprising at least partially neutralized, monoethylenically unsaturated monomers bearing carboxylic acid groups ($\alpha$1) and at least one crosslinker (α3) is provided. Preferably, the aqueous monomer solution is an aqueous solution of partially neutralized acrylic acid, further comprising crosslinkers. In the second step 110 fine particles of a water-absorbent polymer may be added to the aqueous monomer solution. In the third step 120 a polymerization initiator or at least one component of a polymerization initiator system that comprises two or more components is added to the aqueous monomer solution. In the fourth step 130 the monomer solution is applied to a container or a conveyor belt where it is polymerized to a polymer gel. In the fifth step 140 the polymer gel is comminuted, whereby gel particles are obtained. In the sixth step 150 the polymer gel is charged onto the surface of the belt material of a belt dryer at a position $L_0$ and subsequently dried at a temperature of about 120 to 150° C. The polymer gel is discharged from the belt at the discharging position $L_1$ 90. The dried polymer gel is then grinded to obtain particulate water-absorbent polymer particles in the seventh step 160. In the eighth step 170 the ground polymer particles are sized to obtain water-absorbent polymer particles with a well defined particle size distribution. The production process may have further steps at the end or in between of the process flow.

LIST OF REFERENCES 10 conveyor belt system
20 conveyor belt
30, 30' guide roller
35 circled arrow
40, 40' hollow arrow, moving direction
50 charging position $L_0$
60 line (for cut out)
70 polymer gel
80 cooling material
90 discharging position $L_1$
100 first step
110 second step
120 third step
130 fourth step
140 fifth step
150 sixth step
160 seventh step
170 eighth step

The invention claimed is:

1. A process for the preparation of water-absorbent polymer particles, comprising the process steps of
   (i) preparing an aqueous monomer solution comprising at least partially neutralized, monoethylenically unsaturated monomers bearing carboxylic acid groups (α1) and at least one crosslinker (α3);
   (ii) optionally adding fine particles of a water-absorbent polymer to the aqueous monomer solution;
   (iii) adding a polymerization initiator or at least one component of a polymerization initiator system that comprises two or more components to the aqueous monomer solution;
   (iv) decreasing the oxygen content of the aqueous monomer solution;
   (v) charging the aqueous monomer solution into a polymerization reactor;
   (vi) polymerizing the monomers in the aqueous monomer solution in the polymerization reactor;
   (vii) discharging the polymer gel strand out of the polymerization reactor and optionally comminuting the polymer gel thereby obtaining polymer gel particles;
   (viii) drying the polymer gel particles;
   (ix) grinding the dried polymer gel particles thereby obtaining particulate water-absorbent polymer particles;
   (x) sizing the grinded water-absorbent polymer particles; and
   (xi) treating the surface of the grinded and sized water-absorbent polymer particles;
   wherein in process step (viii) the gel particles obtained in process step (vii) are charged onto the surface of the belt material of a belt dryer at a position $L_0$ and are subsequently dried on their way through the belt dryer and wherein the belt material has been cooled before coming into contact with the gel particles; and
   wherein cooling the surface of the belt material is performed by continuously spraying a cooling liquid onto the surface of the belt material.

2. The process according to claim 1, wherein the surface of the belt material of the belt dryer at position $L_0$ has been cooled to a temperature below 160° C. before coming into contact with the gel particles.

3. The process according to claim 1, wherein the surface of the belt material of the belt dryer at position $L_0$ has been cooled to a temperature below 140° C. before coming into contact with the gel particles.

4. The process according to claim 1, wherein the surface of the belt material is cooled by spraying an aqueous additive solution onto the belt material, the additive being a polyalkylene glycol.

5. The process according to claim 4, wherein the concentration of the additive in the aqueous additive solutions is in the range from 0.01 to 20 wt.-%, based on the weight of the aqueous additive solution.

6. The process according to claim 1, wherein the carboxylic acid groups in the polymer gel are neutralized to an extend of less than 70 mol-%.

7. The process according to claim 1, wherein the polymer gel is charged onto the surface of the belt material in process step (viii) by means of a swivel belt.

8. The process according to claim 1, wherein the thickness of the layer of the polymer particles to be dried on the belt dryer is not less than 2 cm and not more than 20 cm.

9. The process according to claim 8, wherein the aqueous additive solution is a mixture of water with a polyalkylene glycol.

10. The process according to claim 1, wherein the belt speed of the belt dryer is not less than 0.005 m/s and not more than 0.05 m/s.

11. The process according to claim 1, wherein the cooling liquid is water.

12. The process according to claim 1, wherein the cooling liquid is selected from alcohols, or mixtures of alcohols with water.

13. The process according to claim 1, wherein the cooling liquid is an aqueous additive solution.

14. The process according to claim 1, wherein the cooling liquid is sprayed onto the belt at least one position at the charging position $L_0$.

* * * * *